US006241967B1

(12) United States Patent
Sachse et al.

(10) Patent No.: US 6,241,967 B1
(45) Date of Patent: *Jun. 5, 2001

(54) PROCESS AND DEVICE FOR THE PRODUCTION OF LIQUID, DISPERSE SYSTEMS

(75) Inventors: Andreas Sachse, Bonhoefferufer 8, 10589 Berlin; Thomas Schneider, 12161 Berlin; Georg Rossling, Oranienburger Chaussee 60, 13465 Berlin, all of (DE)

(73) Assignees: Andreas Sachse; Georg Rossling, both of Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/416,842

(22) PCT Filed: Oct. 13, 1993

(86) PCT No.: PCT/DE93/00997

§ 371 Date: Jul. 10, 1995

§ 102(e) Date: Jul. 10, 1995

(87) PCT Pub. No.: WO94/08626

PCT Pub. Date: Apr. 28, 1994

(30) Foreign Application Priority Data

Oct. 16, 1992 (DE) ................................ 42 35 381
Aug. 18, 1993 (DE) ................................ 43 28 331

(51) Int. Cl.⁷ .......................... A61K 51/00; A61M 36/14
(52) U.S. Cl. .................. 424/9.321; 424/9.3; 424/9.1; 424/450
(58) Field of Search .................. 424/1.11, 1.29, 424/1.65, 9.1, 9.3, 9.321, 9.4, 9.5, 450, 9.51, 9.52; 264/4.3, 13; 252/314

(56) References Cited

U.S. PATENT DOCUMENTS 4,737,323 * 4/1988 Martin et al. ................. 424/450
4,957,939 * 9/1990 Gries et al. .................... 424/9.1
5,008,050 * 4/1991 Cullis et al. ................... 424/450
5,021,236 * 6/1991 Gries et al. .................... 424/9.1
5,078,986 * 1/1992 Bosworth et al. .............. 424/9.1
5,088,409 * 2/1992 Unger ........................... 424/450
5,110,475 * 5/1992 Rössling et al. ............... 210/640
5,228,446 * 7/1993 Unger et al. ................... 424/450
5,230,882 * 7/1993 Unger ........................... 424/9.1
5,393,530 * 2/1995 Schneider et al. .............. 424/450
5,445,810 * 8/1995 Schneider et al. .............. 424/9.4
5,450,847 * 9/1995 Kampfe et al. ................ 128/653.4
5,542,935 * 8/1996 Unger et al. ................... 424/450
5,556,580 * 9/1996 Suddith ........................ 264/4.3
5,626,832 * 5/1997 Schneider et al. ............. 128/653.4

FOREIGN PATENT DOCUMENTS

3933938 * 4/1991 (DE) .
0036676 * 9/1981 (EP) .
0460720 * 11/1991 (EP) .
0535567 * 4/1993 (EP) .
8600238 * 1/1986 (WO) .
9205772 * 4/1992 (WO) .

OTHER PUBLICATIONS

Schneider et al (1994), Drug Development and Industrial Pharmacy, vol. 20, No. 18, pp. 2787–2807, "Large Scale Production of Liposomes of Defined Size by a New Continuous High Pressure Extrusion Device."*

Schneider et al (1995), International Journal of Pharmaceutics, vol. 117, pp. 1–12, "Generation of Contrast–Carrying Liposomes of Defined Size with a New Continuous High Pressure Extrusion Method."*

* cited by examiner

Primary Examiner—Dameron L. Jones
(74) Attorney, Agent, or Firm—Millen White Zelano & Branigan

(57) ABSTRACT

A continuous process for the production of liquid, disperse systems is described, which is characterized in that a pre-dispersion is extruded under a high pressure of 6.6 to 250 MPa sequentially over 1 to 8 filter stages of decreasing pore size between 0.01 and 35 μm, and up to 20 passages per filtration stage can be used.

Further, a device is described which can be used for implementing the process according to the invention.

32 Claims, 2 Drawing Sheets

PROCESS AND DEVICE FOR THE PRODUCTION OF LIQUID, DISPERSE SYSTEMS

This application is a 371 of PCT/DE93/0997 filed Oct. 13, 1993.

The invention relates to a process and a device for the production of liquid, disperse systems.

In addition to the cosmetics industry, there is a great need for processes and devices for the production of disperse systems, particularly in the pharmaceutical industry. This is especially true because so-called pharmaceutical carrier systems ("drug-delivery systems"), which represent disperse systems (especially solid/liquid or liquid/liquid), were developed in the search for new ways to transport pharmaceuticals. For example, emulsions (liquid/liquid) for parenteral feeding or administration of sparingly water-soluble pharmaceuticals and especially liposome suspensions, which can be used as targeted pharmaceutical carriers, can be cited among these.

Due to the hydrophobic interactions, spontaneously sealed lipid vesicles, which are referred to as liposomes, result after phospholipids are dispersed in water. These are spherical or elliptical hollow bodies with one or more lipid double layers ("bilayers"), which include an aqueous phase. Depending on their size, in this case small unilamellar vesicles ([SUV], with radii of 25 to 50 nm) and large unilamellar vesicles ([LUV], with radii of greater than 50 nm up to 10 $\mu$m) are distinguished (Weiner, N., Martin, F., Riaz, M., Drug Dev. Ind. Pharm. 15, 1523–1554 (1989)).

Further, multilamellar liposomes (multilamellar vesicles [MLV]) are known, in which several concentrically arranged bilayer liposomes as well as multivesicular liposomes (multivesicular vesicles [MVV]) are present, which in turn have vesicular structures in their lumens.

The liposomes are suitable for inclusion of both hydrophilic pharmaceuticals and lipophilic pharmaceuticals, in which the extent and site of the inclusion depend on the physicochemical properties of the pharmaceutical and the lipid composition of the liposomes.

As the most important step, all processes for the production of liposomes comprise the dispersion of the lipid or lipid mixture in an aqueous phase. Based on this, all production processes can be classified according to the three main dispersion principles. In this case, "mechanical dispersion", "two-phase dispersion," and "detergent solubilization" are distinguished (New, R. R. C. (Editors), Liposomes: A Practical Approach, Oxford University Press, New York, 1990, p. 33).

In the methods which comprise a "two-phase dispersion," it is particularly the limited solubility of some lipids in organic solvents as well as the great expense involved in removing the solvents used (such as chloroform, methanol, diethyl ether) to lower the residual solvent concentration to tolerable concentrations (toxicity) that are disadvantageous. The "detergent solubilization methods" exhibit the drawback of the residual detergent content, which can be removed from the preparation only with difficulty.

In the so-called "mechanical dispersion process," on the other hand, the use of organic solvents or detergents during the dispersion of the lipid in the water phase is unnecessary. Generally, in this case, first a lipid film is formed by rotary evaporation of an organic solution of the lipid or lipid mixture (for example, in chloroform, methanol or diethyl ether). For complete removal of the residual solvent, freeze-drying under high vacuum for 12–24 hours is then often done. By subsequent addition of an aqueous phase and simple shaking (the so-called hand-shaken method according to Bangham, Bangham, A. D.; Standish, M. M.; Watkins, J. C., J. Mol. Biol. 13, 238–252 (1965)), an MLV suspension is obtained that is extremely heterogeneous with respect to liposome size and lamellarity.

For further processing of corresponding MLV suspensions, there are several processes in which SUV or LUV are generally obtained.

The oldest and most popular method for the production of SUV is the so-called "sonication method" (ultrasonic irradiation method). In this case, MLV are crushed by ultrasonic irradiation (ultrasound wand or ultrasound bath). The liposomes thus obtained have an average diameter of 20 to 60 nm and an inclusion capacity of less than 1%. The drawbacks of these methods are particularly the high heat input, which can lead to decomposition of the lipid or of the pharmaceutical, as well as the difficulty in handling even larger sample amounts in a reproducible manner. With the use of the ultrasound wand, moreover, there exists the drawback of contamination of the samples with titanium fragments, as well as the formation of an aerosol (see the already cited publication by R. R. C. New).

Another method for the production of small unilamellar or oligolamellar liposomes is the "French press method," whose name comes from the high-pressure apparatus (French press) used here. This unit consists of an electric, hydraulic press and a high-pressure cell, which has a maximum capacity of 4 or 40 ml depending on design (New, R. R. C.; see above). The disadvantage to this method is, in addition to the limited volume of the dispersions to be processed, particularly the fact that the finished liposome suspensions are generally contaminated with abrasion residues from the pressure chamber or a portion of uncrushed MNLV, as well as the difficulty in controlling the rise in temperature in the chamber.

So-called high-pressure homogenizers also recently were introduced in liposome technology. Thus, the production of SUV with a minimum-quantity ring slot homogenizer from MLV or lipid dispersions (without prior film formation) has been described (Brandl, M.; Bachmann, D.; Drechsler, M.; Bauer, K. H., Drug Dev. Ind. Pharm. 16, 2167–2191 (1990)).

This process allows the reproducible production of small amounts of homogeneous SUV dispersions with very small average diameters (<50 nm). But particularly the occurrence of equipment wear and tear (ring gap, etc.), as well as the difficulty in controlling the product temperature, are drawbacks in this regard.

In addition to the previously described processes for the production of SUV, there are also several mechanical processes for the production of LUV which also work with use of predispersions (liposomes or lipids).

The oldest of these processes is the so-called "extrusion method." In this process, an MLV dispersion is filtered by hand sequentially through filter holders with polycarbonate filters of decreasing pore size (3.0, 1.0, 0.8, 0.6, 0.4 and 0.2 $\mu$m) at pressures up to 0.35 Mpa (Olson, F.; Hunt, C. A.; Szoka, F. C.; Vail, W. J.; Papahadjopoulos, D., Biochim. Biophys. Acta 557, 9–23 (1979)).

The so-called "LUVET method" (large unilamellar vesicles by extrusion) represents a further development of these extrusion methods (WO86/00238, 1986 and Hope, M. J.; Bally, M. B.; Webb, G.; Cullis, P. R.; Biochim. Biophys. Acta 812, 55–65 (1985)). With this discontinuous process, a coarse lipid or liposome dispersion is repeatedly extruded at pressures of less than 3.5 MPa with two polycarbonate filters, placed one above the another, with pore sizes of less than or equal to 100 nm. In this case, unilamellar liposomes with a diameter of 60 to 100 nm and inclusion volumes of 1 to 3 l of aqueous phase per mol of lipid are obtained. If the liposome suspension below a lipid concentration of about 200 µmol per ml is additionally subjected to several freeze-thaw cycles (freezing of the suspension and subsequent thawing—Cullis, P. R.; Mayer, L. D.; Bally, M. B.; Madden, T. D.; Hope, M. J., Adv. Drug Delivery Rev. 3, 267–282 (1989)), an increase in inclusion efficiency can be noted. With the use of pressures of up to 5.5 MPa, very high lipid concentrations have been processed. In the pressure filter devices used in this technology, the predispersion is added to an infusion chamber located directly over the membrane, the pressure vessel is closed, and then the pressure necessary for filtration is built up using compressed air or nitrogen. The filtrate is removed through a drain and then fed back to the infusion chamber again up to 20 times.

Drawbacks to the extrusion method are the discontinuous operating method, the low working volumes, and the low filtration pressures of the commercially available devices.

High-pressure homogenization with the so-called Microfluidizer™ represents a relatively new process (Mayhew, E.; Lazo, R.; Vail, W. J.; King, J.; Green, A. M., Biochim. Biophys. Acta 775, 169–174 (1984)).

In this method, an MLV dispersion or a coarse, aqueous lipid dispersion is first placed in a tank and forced by a high-pressure pump with a prefilter (5 µm) into a so-called interaction chamber, in which the liquid flow in microchannels is split into two individual streams that then are combined again at high speed. After exiting from the interaction chamber, the dispersion obtained can either be removed or recirculated.

The main disadvantage to this process is the occurrence of metal abrasion in the finished preparations, as well as the fact that a partial loss or decomposition of the lipid is observed (Talsma, H.; Özer, A. Y.; van Bloois, L.; Crommelin, D. J. A., Drug. Dev. Ind. Pharm. 15, 197–207 (1989)). Moreover, the size and lamellarity of the liposomes can be reproducibly adjusted only over a limited range.

In the production of emulsions, simple, fast stirrers, shakers, stirrers with rotor and stator (e.g., ultra turrax), and colloid mills are used. Because of various hardware drawbacks, as well as the poor reproducibility and low degrees of dispersion that are achieved with these devices, particularly the high-pressure homogenization processes, despite the drawbacks associated with them, have gained acceptance in the production of emulsions, in addition to ultrasonic irradiation (on a laboratory scale) (Praveen, T. (Editors): Specialized Drug Delivery Systems, Drugs and the Pharmaceutical Sciences, Vol. 41, Marcel Dekker, Inc., New York, Basel 1990, p. 317 ff). In this case, particularly the ring slot homogenizers from the APV Gaulin company (Lübeck, Germany) or the Microfluidizer™ can be mentioned whose use for, e.g., the production of emulsions for the parenteral feeding is already described (Washington, C.; Davis, S. S., Int. J. Pharm. 44, 169–176 (1988) and Muchtar, S.; Jacobs, G. P.; Benita, S., Tenside [Surfactants] Surf. Det. 26, 347–351 (1989)).

The continuous process for the production of liquid dispersions according to the invention does not have the above-mentioned drawbacks of the previously known process. It is characterized by a predispersion being sequentially extruded under a high pressure of 6.6 to 250 MPa with 1 to 8 filter stages of decreasing pore size between 0.01 and 35 µm, and up to 20 passages per filtration stage can be used.

The process according to the invention is preferably carried out at a working pressure of 7 to 80 MPa. Extrusion can be done here in each filtration stage over one or a combination of 2–4 filters of the same or different pore sizes in each case. In this way, membrane filters, such as, for example, polycarbonate membranes (surface filters) from, e.g., the Nucleopore company (Tübingen) are used in most cases.

In contrast to the previously known processes, however, other filters of corresponding differential-pressure strength made of widely varying materials and in widely varying geometries (such as, for example, filter disks, filter cups, or filter candles) are also suitable for carrying out the process according to the invention. Suitable filters are metal or polymer membranes or inorganic materials such as, for example, glass fiber or anopore$^R$ membranes (Anotec company, Banbury Oxon, England). Examples of suitable polymer materials are filters made of polytetrafluoroethylene (PTFE), polypropylene (PP), polyvinylidene fluoride, or cellulose esters, such as, for example, cellulose acetate.

It was already mentioned that the invention relates not only to a process for the production of liquid dispersions, but also a device for implementing this process. This device, which can be called a continuously operating high-pressure extrusion apparatus (see FIG. 1), is characterized by a storage vessel (1), whose drain line leads to a high-pressure pump (2), which is designed to build up working pressures of a maximum of 250 MPa. On the output side, this pump is connected to a filter holder (6), whose purpose is to remove the filters used according to the invention from which the product is either recirculated and/or removed to the storage vessel via a drainpipe (7).

The high-pressure pump is preferably designed to build up working pressures of a maximum of 80 MPa. A prefilter can optionally also be attached between the high-pressure pump and the filter holder, which is intended to receive filters with an average pore size of 2 to 35 µm. Further, the device according to the invention can also be equipped with ventilating devices and/or temperature and pressure gauges.

Suitable pumps for the device according to the invention are, for example, pneumatic or hydraulic reciprocating pumps (for example, Maximator$^{(R)}$, Schmidt Company, Kranz & Co., Zorge, Germany). Suitable pumps are usually those which have a transformation factor of about 50 to 750 and thus can generate working pressures of between 5 and 300 MPa from 0.1 to 0.4 MPa of input pressure (air or nitrogen). The devices according to the invention should be equipped with a control valve (3), by means of which the pressure to be used in the process according to the invention can be specifically controlled. Even large amounts of dispersions with high concentrations of disperse phase (for example 500 mg of lipid per ml of aqueous phase) and consequently high viscosity (gel-like) can then also be extruded at high pressure, which is generally not possible in the case of the previously known processes. The product flows that result in this case are generally between 0.1 and 10 liters per minute, preferably 0.15 to 3 liters per minute.

The problem of clogging of the filter that occurs with other methods is further eliminated by the high pressures that can be used in the process according to the invention, thus eliminating down times in the process for changing the filter.

The storage vessel used in the device according to the invention can be configured in such a way that it can be tempered, and the pipes can be metal tubes or hose lines. As an alternative to this, product recycling can also be done via a two-chamber storage tank or a liquid coil, with heat exchange if appropriate.

If the device is to be used for the production of pharmaceutical preparations, it must be possible to sterilize all its parts that come into contact with the product, and these parts must be resistant to the solvent used in it. Preferably, the device is made from materials which allow heat sterilization.

In contrast to most previously known devices, the high-pressure extrusion apparatus according to the invention makes it possible to produce liquid dispersions continuously and in substantial amounts, thus significantly reducing production expense for the dispersion and considerably improving the economic efficiency of the process.

Thus, the apparatus used in the embodiments has, for example, filter holders, which allow for the use of membrane filters of 47 mm diameter. The pressurization capacity of the filter holder used here is 80 MPa. This device makes it possible to produce dispersions quickly in the range of 100 to 1000 ml (the dead volume of the unit is about 10 ml). With two filters with a diameter of 47 mm and with a pore size of less than or equal to 100 nm are used, flows can be achieved with this device that are considerably above 150 ml per minute.

When the apparatus is properly designed, however, fabrication on an industrial and production scale is also possible with no negative impact on product properties. When the device is properly designed (pumping capacity, filter geometry, pipe connections, etc.), the achievable flow rate can be increased to far above 3 l per minute with the corresponding units. As an alternative, however, it is also possible to design such units for very small product amounts where this is desired for, e.g., economic reasons.

In the case of devices in which recycling of the product is to take place after completion of the first dispersion, it is often advisable for the dispersion to be collected first in a two-chamber system, with the latter being fed back into the unit by merely opening an appropriate valve again. Compared to direct recirculation, this two-chamber system offers the advantage that first the entire amount of the dispersion is always subjected to the shearing process and no mixing of undispersed and dispersed phase occurs. The same effect can also be achieved by recirculating the dispersion through a liquid coil that holds the entire volume of the batch to be processed. Tempering of the dispersion over the outside walls of the corresponding coils can also be done simultaneously here.

The device according to the invention is not only suitable for implementing the process according to the invention, but can also be of benefit when using lower pressures in the range of 1 to 6.6 MPa.

The processes for the production of liquid dispersions according to the invention that can be implemented by the device of the invention are of special importance in the liposome technologies for pharmaceuticals and cosmetics since they allow economical production of large amounts of liposomes with reproducible properties (such as, for example, inclusion amount, liposome size, and liposome lamellarity) in pharmaceutical quality (for example, sterility and absence of pyrogen).

The process according to the invention makes it possible to produce unilamellar or multilamellar liposomes over a wide range of limits (average diameter generally 25 nm to 5 $\mu$m). The size and homogeneity of the size distribution, as well as the lamellarity of the liposomes contained here, are, i.a., a function of the type of filter used and pore size, the filtration pressure (working pressure), the number of passages through the device, the type of lipid and lipid concentration, and the type and amount of the pharmaceutical used. By means of the usual preliminary tests, such as are familiar to one skilled in the art, formulations with very narrow size and lamellarity distributions can be obtained by properly selecting these parameters.

In the case where liposomes are formed with the help of the process according to the invention, the same lipid components can be used as in the other processes of this type. Such lipids are generally phospholipids, such as, for example, phosphatidylcholine, phosphatidylethanolamine, phosphatidylglycerol, phosphatidylserine, phosphatidic acid, phosphatidylinositol, or sphingolipids. Moreover, as additional components, sterols, such as, for example, cholesterol or else other components, such as fatty acids (e.g., stearic acid, palmitic acid), dicetyl phosphate, or cholesterol hemisuccinate, can be used. When amphiphilic substances, such as, for example, hexadecylpoly(3)glycerol, dialkylpoly (7)glycerol ether, and alkyl glucosides are used, so-called niosomes, which are liposomes made of nonionogenic vesicle formers, are obtained.

It is possible to encapsulate liposomally both hydrophilic and lipophilic pharmaceuticals by means of the device according to the invention and the process according to the invention. Suitable active ingredients are, for example, vitamins, hormones, antifungal agents, anti-allergenic agents, antiphlogistic agents, antihypertensive agents, anti-arrhythmic agents, antibiotics, antiviral agents, anxiolytic agents, cytostatic agents, immunomodulators, contraceptives, peptides, proteins, and sedatives.

In the case of hydrophilic pharmaceuticals, the latter are generally dissolved in the aqueous phase that is used for the production of the predispersion and subjected to the process according to the invention after the predispersion is produced. In this case, surprisingly enough, liposomes with especially high inclusions can be obtained.

Thus, the process according to the invention proves to be especially suitable for, i.a., encapsulating contrast media for x-ray diagnosis (or computer tomography) and NMR [nuclear magnetic resonance] diagnosis, which were only inadequately encapsulated using the previously known mechanical dispersion methods. In the case of the inclusion of iodine-containing x-ray contrast media (RKM), high inclusion capacities can also be achieved even in the case of small liposome diameters and relatively small lipid concentrations. By combination with one or more freeze-thaw cycles (freezing and thawing), a further increase in inclusion can be achieved. Especially suitable examples of corresponding x-ray contrast media of the type of triiodobenzoic acid are iopromide, iohexol, iopamidol, ioversol, iopentol, ioxaglat, 3-carbamoyl-5-[N-(2-hydroxyethyl)-acetamido]-2, 4,6-triiodobenzoic acid-[(1RS,2SR)-2,3-dihydroxy-1-hydroxymethylpropyl]-amide and iotrolan.

In the case of the inclusion of contrast media for NMR diagnosis, the process according to the invention proves superior with respect to the inclusion capacities that can be achieved compared to all previously described mechanical processes. By mere high-pressure extrusion, extremely high inclusions can be obtained which, surprisingly enough, cannot be significantly further increased by additional freeze-thaw cycles. In this case, NMR contrast media that are especially suitable for encapsulation are Gd-DTPA, Gd-EOB-DTPA, Gd-BOPTA, Gd-DOTA, gadobutrol, and Mn-DPDP (U.S. Pat. No. 4,957,939, U.S. Pat. No. 5,021,236 and Shuhmann-Giampieri, G., Inv. Radiol. 28, (1993) in press).

As an alternative to this, suitable water-soluble substances can also be encapsulated with so-called active loading techniques (remote loading). In this connection, for example, first pharmaceutical-free liposomes are produced by a high-pressure extrusion technique which are then loaded, e.g., via a pH gradient, with the substance to be encapsulated (Cullis, P. R.; Mayer, L. D.; Bally, M. B.;

Madden, T. D.; Hope M. J., Adv. Drug Delivery Rev. 3, 267–282 (1989)).

To encapsulate lipophilic substances, the corresponding active ingredient in the process of the invention can be encapsulated by being dissolved or dispersed in the lipid predispersion or by being subsequently stirred in a finished liposome suspension. Such pharmaceuticals can be modified pharmaceutical molecules (amphiphilic substances) which can act directly as liposome membrane components through corresponding chemical modification.

As with the previously existing liposome preparation processes, in lipophilic pharmaceuticals the process can start with quantitative encapsulation of the respective components, as long as a critical pharmaceutical/lipid ratio is not exceeded. As a consequence, the process according to the invention also proves to be especially suitable here since even extremely high concentrations of lipophilic pharmaceuticals can be dispersed owing to the fact that extremely high lipid concentrations (>400 mg/ml) can be processed.

The process according to the invention is distinguished by very good reproducibility of the liposome properties produced compared to the previously described production methods. Thus, for example, it can be proven in the repeated production of contrast medium-containing liposomes under identical conditions that the liposomes produced have only small fluctuations with respect to their properties (particularly inclusion, size, and size distribution). This reproducibility of the process is not negatively affected by the scaling-up of production.

The process according to the invention is also especially suitable for being carried out under aseptic conditions. This is particularly important in those cases where the desired liposomes cannot be subjected to any terminal sterile filtration (0.2 $\mu$m) because of their size. For aseptic production, sterilized, depyrogenated devices, as well as sterile and pyrogen-free starting substances are to be used, and work is to be performed in clean rooms of the corresponding clean room classes. In all other cases (i.e., final extrusion of less than or equal to 0.6 $\mu$m), the end product can be sterilized by filtration in most cases (e.g., 0.2 $\mu$m). Moreover, the process according to the invention offers the possibility of removing germs from the start by extrusion using filters of suitable pore size (less than or equal to 0.6 $\mu$m), thus making additional sterilization by filtration unnecessary.

The process according to the invention is also especially suitable for the production of liposomes that are stable in storage. In the case of storing iopromide-containing liposomes in which the unencapsulated iopromide portion is not separated, no reduction in pH or inclusion and no change in the average diameter can be noted, for example, after three months of storage in a refrigerator.

With respect to the production of emulsions, the process according to the invention offers for the first time the possibility of continuously producing large amounts of emulsion with reproducible properties. The advantages (liposome production) of the high-pressure extrusion process of the invention cited above basically also exist in emulsion production. The previously undescribed use of filter extrusion in this area, which was first opened up by the high-pressure extrusion process according to the invention, makes possible the flexible production of emulsions over a broad range of sizes (100 nm–20 $\mu$m mean diameter of the dispersed phase) without major hardware cost. The process is also distinguished in this application by the fact that large amounts of inner phase can be processed and in most cases, direct production (without predispersion) is also possible.

Depending on the desired purpose, two-phase or multiphase emulsions (e.g., W/O, O/W, W/O/W or O/W/O [W=water, O=oil]) can be produced by this process. Vegetable oils, such as soybean oil, castor oil, safflower oil, or olive oil, for example, can be used here as oil phases. Suitable emulsifiers are, for example, egg and soybean lecithins or pure phospholipids from such fractions. Moreover, nonionic surfactants, such as, e.g., higher fatty alcohols, sorbitan fatty acid ester, or polyethylene glycol ether or ester can also be used. The water phase can consist of pure water (p.i. or pure) or aqueous solutions of various buffers or salts (e.g., NaCl, KCl) and can also contain additives, such as, for example, glycerol. Moreover, emulsions for parenteral feeding can additionally contain sugars, such as glucose and xylitol, as well as additional salts, such as sodium dihydrogen phosphate, magnesium chloride, or zinc acetate. In addition, fats, such as, e.g., mid-chain triglycerides can also be present in the emulsion.

Further, in one or both phases, pharmaceuticals can be dissolved or suspended even before emulsion production or after completion of emulsion production, and can be worked in as in the case of the process described in the literature. In this case the corresponding hydrophilic or lipophilic active ingredients can belong, for example, to the class of substances cited above (liposome production).

EXAMPLES

The following embodiments are used for a more detailed explanation of the device according to the invention and the process according to the invention.

The abbreviations used here are the following:

Chol: Cholesterol, powdered cholesterol, E. Merck Company, Darmstadt

DCP: dicetyl phosphate, sigma,

EPC: egg phosphatidylcholine, lipoid E 100, Lipoid KG Company, Ludwigshafen

EPS: egg phosphatidylserine, lipoid EPS, Lipoid KG company

PCS: photon correlation spectroscopy—process for measuring particle sizes under 1 $\mu$m SPA: soybean phosphatidic acid, Lipoid SPA, Lipoid KG Company SPC: Soybean phosphatidylcholine, Lipoid S 100, Lipoid KG Company SPE: Soybean phosphatidylethanolamine, Lipoid SPE SPG: Soybean phosphatidylglycerol, Lipoid SPG, Lipoid KG Company SS: stearic acid, Fluka, CH-Buchs

A.) Embodiments Pertaining to the Device According to the Invention

Example A 1

Figure 1:
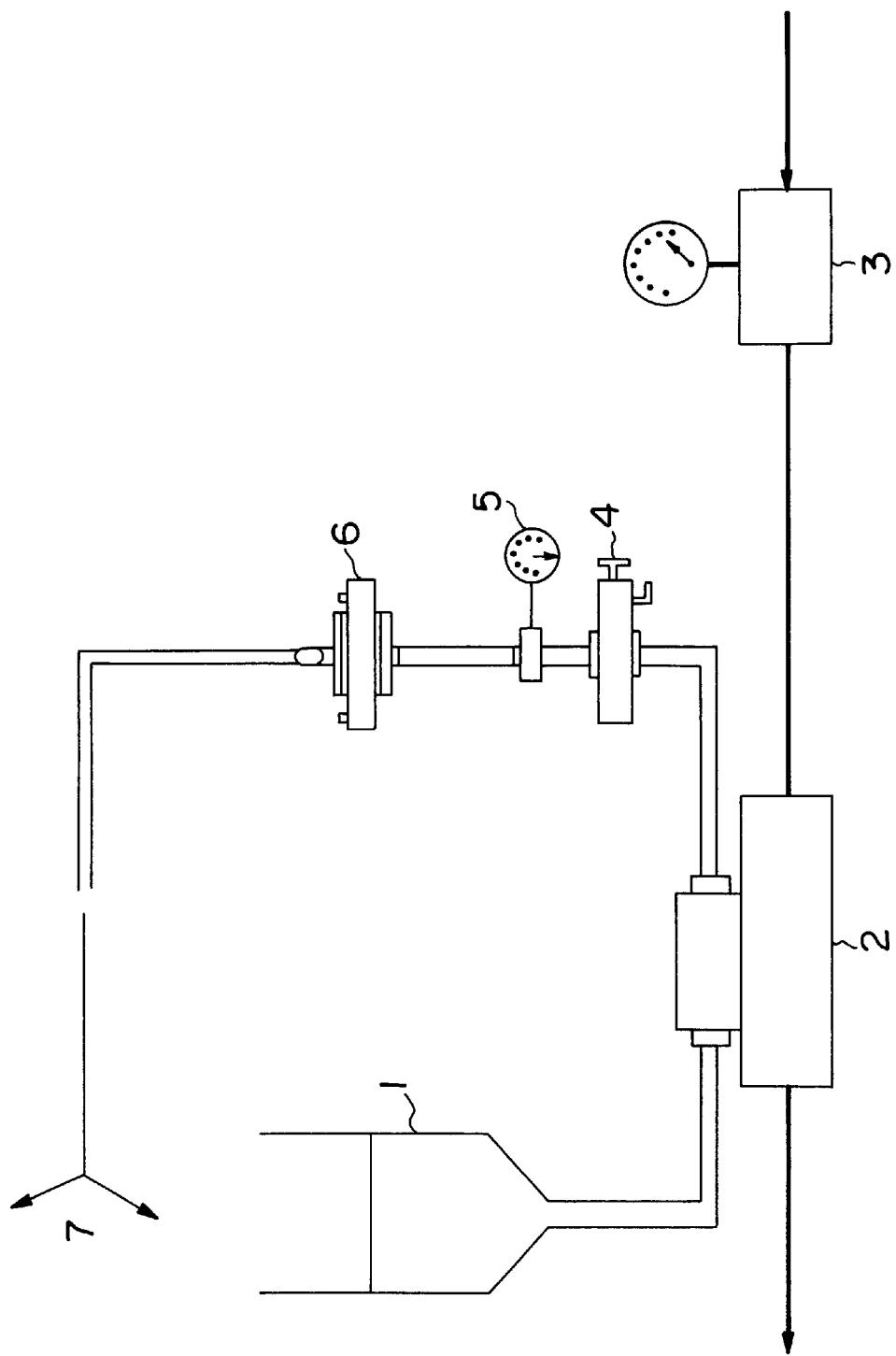
FIG. 1 illustrates an apparatus according to the invention as further described in Example A1.

The device is a continuous-operation high-pressure extrusion apparatus which is diagrammatically represented in FIG. 1.

It consists of a storage vessel (1) which can be tempered and which is connected by a pipe connection to a piston pneumatic pump (2) having a transformation factor of about 250. The piston pneumatic pump is operated by means of nitrogen, and the input pressure is controlled by an intake valve (3).

A pipe connection leads from the high-pressure pump via a ventilating valve (4) and a pressure gauge (5) to a high-pressure filter holder (6), which is suitable for receiving membrane filter disks with a diameter of 47 mm. The dispersion leaving the filter holder is removed via a hose connection (7), which is used optionally for product removal or for product recycling to storage vessel (1).

Example A2

Figure 2:
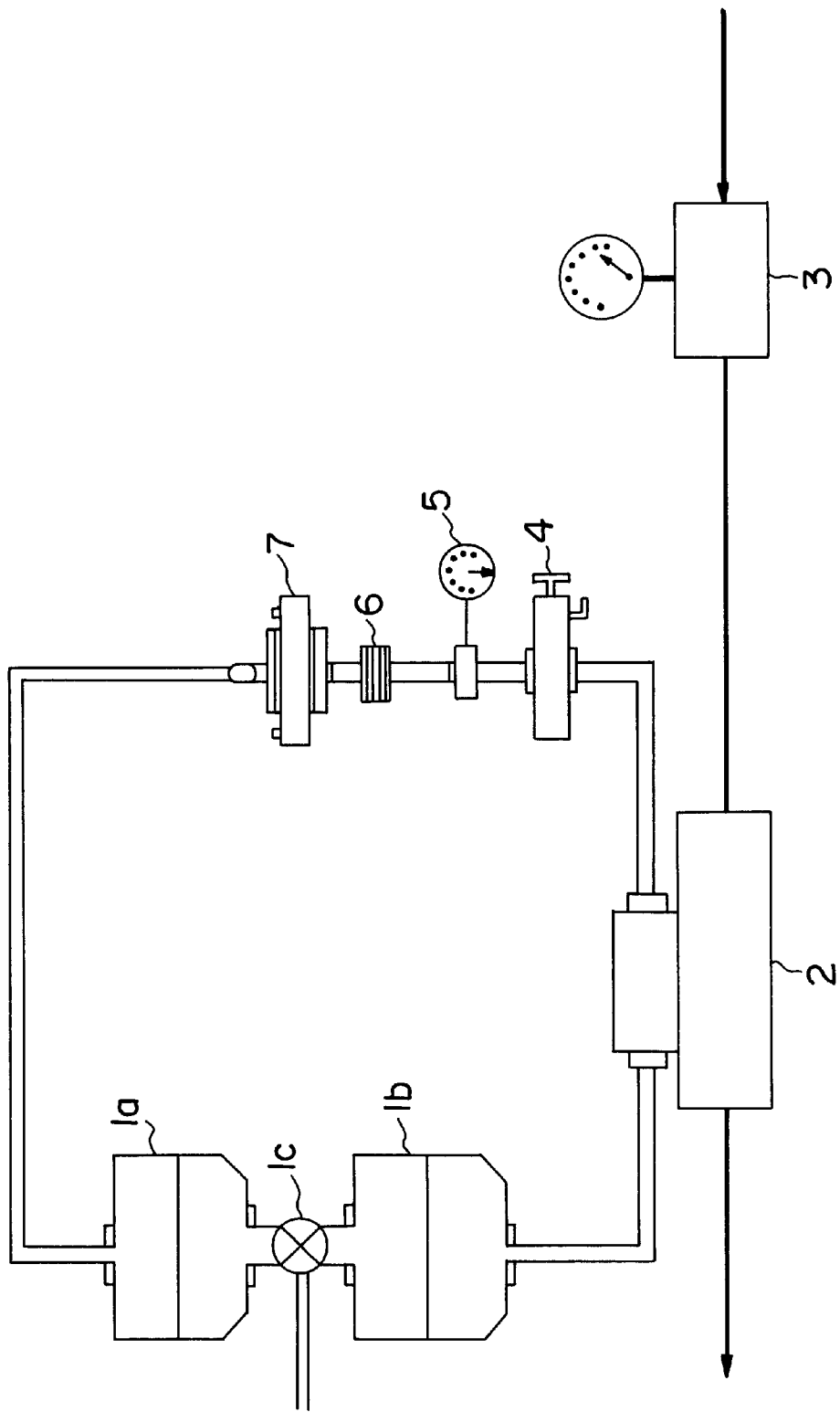
FIG. 2 illustrates an apparatus according to the invention as further described in Example A2.

This device diagrammatically represented in FIG. 2 is also a continuous-operation high-pressure extrusion apparatus.

It is different from the apparatus represented in FIG. 1 in that a metal cup prefilter (6) with a pore diameter of, for example, 35 μm, is incorporated behind pressure gauge (5).

Another difference in the apparatus shown in FIG. 1 lies in the fact that the hose connection exiting from filter holder (7) leads to a two-chamber storage vessel (1). The outlet of the upper of two vessels (1a) is equipped with a three-way valve (1c), which allows it to remove completely or partially the dispersion contained in it or to feed back to the high-pressure extrusion process via lower vessel (1b).

B.) Embodiments Pertaining to the Process According to the Invention

Preliminary remark: In the embodiments below, the average vesicle diameter is determined by PCS (submicron particle sizer autodilute model 370, Nicomp Instr. Corp., Goleta, Calif.).

Example B 1: Production of a Liposome Suspension with 50 mg of SPC/ml 5 g of SPC is dissolved at 50° C. in a rotary evaporator in ethanol and then concentrated into a film by evaporation.

The film obtained is mixed with 100 ml of 20 mmol tris-HCl buffer (pH=7.5) and, after 15 minutes of swelling, is removed by being shaken by hand for at least 2 minutes. The predispersion thus obtained is sequentially filtered with the apparatus according to the invention at a working pressure of between 3 and 10 MPa 5 times each over 2 polycarbonate membranes of decreasing pore size (5.0, 1.0, 0.4, 0.2, 0.1, 0.05 and 0.03 μm).

The liposome suspension obtained is slightly opalescent, and the liposomes have an average diameter of 64 nm.

Example B 2: Production of a Liposome Suspension with 200 mg of SPC/ml

Production in the same way as Example B 1 but using 20 g of SPC in film formation.

The liposome suspension obtained is slightly opalescent, and the liposomes have an average diameter of 73 nm.

Example B 3: Production of a Liposome Suspension with 400 mg of SPC/ml

Production in the same way as Example B 1 but using 40 g of SPC in film formation.

The liposome suspension obtained has a gel-like consistency, and the liposomes have an average diameter of 74 nm.

Example B 4: Production of a Liposome Suspension with 50 mg of SPC/Chol/SPG (molar ratio 6:3:1) per ml Production in the same way as Example B 1 but using 5 g of the lipid mixture for film formation. The liposome suspension obtained is highly transparent to slightly opalescent, and the liposomes have an average diameter of 72 nm.

Example B 5: Production of a Liposome Suspension with a Reduced Number of Extrusion Steps Production and make-up are done in the same way as Example B 4 but with the extrusion stages reduced to 0.4, 0.1, and 0.03 μm. The liposome suspension obtained is highly transparent to slightly opalescent, and the liposomes have an average diameter of 68 nm.

Examples B 6–B 18: Use of Various Lipids and Lipid Mixtures

Placebo liposomes with different lipid compositions are produced as described below:

- The production of a lipid film is done by rotary evaporation of an organic lipid solution (ethanol, methanol or chloroform/ethanol—depending on solubility) at elevated temperature (e.g., 50° C.).
- The lipid film is dispersed with buffer solution above the phase transition temperature of the lipid mixture used (swelling time at least 15 minutes, shaking by hand for at least 2 minutes)
- The sequential extrusion of the predispersion (MLV) is done over filters of decreasing pore size (5.0; 1.0; 0.4; 0.2; 0.1; 0.05 and optionally 0.03 μm—5 filter passages each—at elevated temperature if appropriate).

In these examples (B 6–B 18), in each case two polycarbonate filters placed one above the other are used per filter size, and the final extrusion is done over a 0.05 μm filter. After extrusion has been completed, the liposome suspensions are sterilized by filtration (cellulose acetate membrane, 0.2 μm). The lipid concentration used in each case is 50 mg/ml. 100 ml batches in buffer (20 mmol of tris (hydroxymethyl)-aminomethane, pH 7.5, named tris-buffer hereinafter) are produced.

TABLE 1

Average Diameter of High-Pressure-Extruded Liposomes of Different Lipid Composition (Examples B 6 - B 18)

| Lipid Mixture | Molar Composition | Average Diameter [nm] |
| --- | --- | --- |
| SPC | | 75 |
| EPC | | 86 |
| SPC:Chol | 9.1 | 80 |
| SPC:Chol | 7.3 | 83 |
| SPC:Chol | 5:5 | 93 |
| SPC:SPE | 9:1 | 93 |
| SPC:EPS | 9:1 | 78 |
| SPC:SPG | 9:1 | 65 |
| SPC:SPA | 9:1 | 66 |
| SPC:SS | 9:1 | 90 |
| SPC:DCP | 9:1 | 91 |
| SPC:Chol:SPG | 6:3:1 | 79 |
| SPC(hydrogenated): Chol:SPG | 6:3:1 | 101 |

Examples B 19–B 22: Batches with Different Lipid Concentrations

Batches consisting of pure SPC and tris-buffer with lipid concentrations of 50, 100, 200 and 400 mg/ml are produced as described under Examples B 6–B 18. The final stage of the extrusion was done with a pore size of 0.03 μm. The values obtained are listed in Table 2.

TABLE 2

Liposome Size as a Function of Lipid Concentration Used
(Examples B 19 - B 22)

| Lipid Concentration [mg/ml] | Average Diameter [nm] |
|---|---|
| 50 | 64 |
| 100 | 70 |
| 200 | 73 |
| 400 | 74 |

Example B 23–B 29: Influencing of the Resulting Vesicle Diameters by the Pore Size of the Filter Used Batches are produced and characterized as under examples B 6–B 18, but with the difference that the pore size of the final extrusion step is varied in each batch. The final pore sizes in each case are 5.0, 1.0, 0.4, 0.2, 0.1, 0.05 and 0.03 μm. A mixture of SPC, Chol, and SPG (6:3:1) in tris-buffer is used as a lipid. The results are summarized in Table 3.

TABLE 3

Vesicle Diameter as a Function of Filter Pore Size
(Examples B 23 - B 29)

| Filter pore size of the final extrusion step [μm] | Average diameter [nm] |
|---|---|
| 5.0 | 403 |
| 1.0 | 268 |
| 0.4 | 191 |
| 0.2 | 118 |
| 0.1 | 106 |
| 0.05 | 79 |
| 0.03 | 72 |

Examples B 30–B 33: Influence of the Number of Passages on Average Vesicle Diameter Four batches are produced and characterized as described under examples B 6–B 18, but with a different number of passages in each case (1, 3, 5 and 10) in each extrusion stage. A mixture of SPC, Chol, and SPG (6:3:1) in tris-buffer is used as a lipid. All batches are subjected to a 3-stage extrusion process by membranes with 0.4, 0.1 and 0.03 μm pore size. The results are presented in Table 4.

TABLE 4

Influence of the Number of Passages

| Number of passages per filter stage | Average diameter [nm] |
|---|---|
| 1 | 104 |
| 3 | 101 |
| 5 | 91 |
| 10 | 70 |

Example B 34: Production of a Liposome Suspension without Preceding Film Formation (Direct Dispersion)

A 100 ml batch consisting of SPC:Chol:SPG (6:3:1) in tris-buffer with a lipid concentration of 50 mg/ml is produced. Without a film first being formed, the lipids are weighed directly into a 100 ml graduated cylinder and mixed with tris-buffer at 70° C. After swelling (30 minutes), they are dispersed with an Ultraturrax for 30 minutes at 13,500 rpm at the same temperature and the extruded as described under Examples B 6–B 18. The ind product has an average diameter of 60 nm with a variation coefficient 25%.

Example B 35: Extrusion Using One Filter Pore Size (0.1 μm)

A 100 batch consisting of EPC in tris-buffer with a lipid concentration of 100 mg/ml is produced. Without preceding film formation, the lipid is weighed directly into a 100 ml graduated cylinder and mixed with tris-buffer at room temperature. After swelling (15 minutes), the mixture is dispersed with an Ultraturrax for 10 minutes at 13,500 rpm at the same temperature and then extruded 10 times each over two 0.1 μm polycarbonate filters placed one above the other. The end product has an average diameter of about 120 nm with a variation coefficient of 32%.

Example B 36: Production of a Large-Scale Batch (1 l of liposome suspension) with High Rates of Flow A 1000 ml batch consisting of SPC in tris-buffer with a lipid concentration of 100 mg/ml is produced. Without a film first being formed, the lipid is weighed directly into a 1000 ml graduated cylinder and mixed with tris-buffer at room temperature. After swelling (15 minutes), the mixture is dispersed with an Ultraturrax for 10 minutes at 13,500 rpm at the same temperature and then extruded 10 times each sequentially over two polycarbonate filters (1.0–0.2 and 0.1 μm) placed one above the other.

In this case, the rate of flow is about 500 ml/minute, regardless of the pore size of the membranes used.

The liposomes obtained after 10 passages over the final filter combination (0.1 μm) have an average diameter of about 110 nm with a variation coefficient of 30%.

Example B 37: Production of a Batch with High Lipid Concentration (500 mg/ml)

A 100 ml batch consisting of SPC in tris-buffer with a lipid concentration of 500 mg/ml is produced. Without a film first being formed, the lipid is weighed directly into a 100 ml graduated cylinder and mixed with tris-buffer at room temperature. After swelling (30 minutes), the mixture is dispersed with an Ultraturrax for 10 minutes at 13,500 rpm at the same temperature, and a gel-like consistency is obtained. This gel is then extruded 2 times each sequentially over two polycarbonate filters (1.0–0.2 and 0.1 μm) placed one above the other, without which the membranes clogged.

The liposomes (gel) obtained after 2 passages over the final filter combination (0.1 μm) have an average diameter of about 180 nm with a variation coefficient of 41%.

Example B 38: Production of a Batch Using Polytetrafluoroethylene (PTFE) Filters A 100 ml batch consisting of SPC in tris-buffer with a lipid concentration of 100 mg/ml is produced. Without a film first being formed, the lipid is weighed directly into a 100 ml graduated cylinder and mixed with tris-buffer at room temperature. After swelling (15 minutes), the mixture is dispersed with an Ultraturrax for 10 minutes at 13,500 rpm at the same temperature. Then, this predispersion is extruded 10 times each sequentially with two PTFE filters (5.0–1.2 and 0.2 μm) placed one above the other.

The liposomes obtained after 10 passages over the final filter combination (0.2 μm) have an average diameter of about 210 nm with a variation coefficient of about 30%.

Example B 39: Production of a Batch Using a Metal (Cup) Filter (5 µm)

A 1000 ml batch consisting of SPC in tris-buffer with a lipid concentration of 100 mg/ml is produced. Without a film first being formed, the lipid is weighed directly into a 1000 ml graduated cylinder and mixed with tris-buffer at room temperature. After swelling (15 minutes), the mixture is dispersed with an Ultraturrax for 10 minutes at 13,500 rpm at the same temperature and then extruded 10 times each over a metal (cup) filter with a nominal pore size of 5 µm.

The liposomes obtained after 10 passages have an average diameter of about 1.4 µm with a variation coefficient of about 80%.

Example B 40: Production of Niosomes

A 100 ml batch consisting of 4 g of VolpoN3 (polyoxyethylene glycol lauryl alcohol) and 1 g of cholesterol in tris-buffer is produced. Without a film first being formed, the lipids are weighed directly into a 100 ml graduated cylinder and mixed at room temperature with tris-buffer. After swelling (15 minutes), they are dispersed with an Ultraturrax for 10 minutes at 13,500 rpm at the same temperature and then extruded sequentially 5 times each over two polycarbonate filters of decreasing pore size (5.0–0.2 and 0.05 µm) placed one above the other. The end product has an average diameter of 53 nm with a variation coefficient of 33%.

Examples B 41–B 44: Inclusion of Iopromide Using Various Production Methods 100 ml liposome suspensions are produced as described in Examples B 6–B 18, which contain the water-soluble, non-ionic x-ray contrast medium iopromide. The iodine concentration in the end product is 100 mg/g, and the lipid concentration 160 mg/g. SPC, Chol, and SPG at a molar ratio of (6:3:1) are used as lipids. Ultravist(R) 370, diluted with tris-buffer, is used as starting solution. The pore size of the final extrusion stage is 0.1 µm. The production processes are distinguished as follows:

B 41. Process as described under Example B 6, extruded at room temperature (RT).

B 42. Process as described under Example B 41, extruded at 70° C.

B 43. Process as described under Example B 6, but after extrusion with 0.4 µm pore size, the batch is subjected to 3 freeze-thaw cycles. Freezing is done in a glass vial in methanol/dry ice at −70 to −80° C., and thawing is done in a water bath at +70° C. It is extruded at room temperature.

B 44. Process as described under B 43, but extrusion at 70° C.

To characterize the liposomes produced, the inclusion is determined by means of equilibrium dialysis with photometric evaluation, as well the average vesicle diameter with PCS. The average values and variation coefficients of the results from three batches each are summarized in Table 5.

TABLE 5

Properties of Iopromide-Containing Liposomes

| Example | Average Diameter [nm] | Inclusion [%] |
|---|---|---|
| 41 | 118 | 34.1 |
| 42 | 107 | 34.0 |
| 43 | 117 | 45.1 |
| 44 | 109 | 40.8 |

Examples B 45–B 49: Iopromide Inclusion and Vesicle size as a Function of the Pore Size of the Final Extrusion Step Batches are produced and characterized as under Example B 43, but with the difference that the pore size of the final extrusion step is varied in each batch. The final pore sizes in each case are 1.0, 0.4, 0.2, 0.1, and 0.05 µm. The freeze-thaw cycles are carried out after extrusion through 5.0 µm. The lipid concentration is 150 mg/ml. The average values and variation coefficients of the results from three batches each are summarized in Table 6.

TABLE 6

Properties of Iopromide-Containing Liposomes as a Function of Pore Size

| Example | Pore Size | Average Diameter [nm] | Inclusion [%] |
|---|---|---|---|
| 45 | 1.0 | 211 | 50.6 ± 1.5 |
| 46 | 0.4 | 207 | 50.3 ± 1.5 |
| 47 | 0.2 | 164 | 45.0 ± 0.5 |
| 48 | 0.1 | 117 | 40.6 ± 0.8 |
| 49 | 0.05 | 87 | 34.2 ± 0.5 |

Examples B 50–B 53: Iopromide Inclusion and Vesicle Size as a Function of Lipid Concentration Batches are produced and characterized as under Example B 43, but with the difference that various lipid concentrations (50, 100, 150 and 160 mg/ml) are used. The average values and variation coefficients of the results from three batches each are summarized in Table 7.

TABLE 7

Properties of Iopromide-Containing Liposomes as a Function of Lipid Concentration

| Example | Lipid Concentration [mg/g] | Average Diameter [nm] | Inclusion [%] |
|---|---|---|---|
| 50 | 50 | 116 | 19.3 ± 1.2 |
| 51 | 100 | 115 | 27.9 ± 0.6 |
| 52 | 150 | 104 | 40.2 ± 1.1 |
| 53 | 160 | 117 | 45.1 ± 1.9 |

Example B 54: Three-Month Stability of Iopromide Liposomes

To evaluate the stability of iopromide liposomes, a 3-part batch is examined with respect to pH, inclusion, and vesicle size after 3 months of storage in a refrigerator. In the case of the stored samples, the unencapsulated iopromide portion is not removed before storage, i.e., the extruded liposomes are stored directly.

Table 8 below shows the properties of the corresponding liposomes at the respective times.

TABLE 8

Stability of Iopromide Liposomes

| Batch | pH after production | pH after 3 months | Inclusion (%) after production | Inclusion (%) after 3 months | Avg. Diam. VK (nm/%) after 3 months | Avg. Diam. VK (nm/%) after production |
|---|---|---|---|---|---|---|
| a | 7.3 | 7.2 | 39.6 | 38.4 | 99/32 | 101/30 |
| b | 7.2 | 7.2 | 41.4 | 40.8 | 107/30 | 114/33 |
| c | 7.2 | 7.2 | 39.5 | 40.3 | 107/36 | 111/36 |
| mean: | 7.2 | 7.2 | 40.2 | 39.8 | 104/33 | 109/33 |

VK = variation coefficient

Examples B 55–B 57: Inclusion of Gd-DTPA Using Various Production Methods 100 ml liposome suspensions are produced as described under Examples B 6–B 18, which contain the water-soluble, ionic MRT-contrast medium gadopentetic acid-dimeglumine salt (called simply Gd-DTPA hereinafter). The Gd concentration in the end product is 180 $\mu$mol/g, and the lipid concentration is 150 mg/g. SPC and Chol are used as lipids at a molar ratio of (7:3). Magnevist$^{(R)}$ diluted with water at 1:1 is used as a starting solution. The pore size of the final extrusion stage is 0.1 $\mu$m. The production processes are distinguished as follows:

B 55. Process as described under Example B 6, extruded at room temperature.

B 56. Process as described under Example B 6, extruded at 70° C.

B 57. Process as described under Example B 6, but the batch is subjected to 3 freeze-thaw cycles after extrusion through 0.4 $\mu$m pore size. Freezing is done in a glass vial in methanol/dry ice at −70 to −80° C., and thawing is done in a water bath at +70° C. It is extruded at room temperature.

To characterize the liposomes produced, the inclusion is determined by means of equilibrium dialysis and inductively-coupled-plasma-atomic-emission-spectrometry (ICP-AES), as well as the average vesicle diameter with PCS. The average values and variation coefficients of the results from three batches each are summarized in Table 9.

TABLE 9

Properties of Gd-DTPA-Containing Liposomes

| Example | Average Diameter [nm] | Inclusion [%] |
|---|---|---|
| 55 | 110 | 44.2 ± 0.5 |
| 56 | 103 | 47.9 ± 0.8 |
| 57 | 101 | 49.5 ± 5.1 |

Example B 58–B 60: Gd-DTPA Inclusion and Vesicle Size as a Function of the Pore Size of the Final Extrusion Step Batches are produced and characterized as under Example B 57, but with the difference that the pore size of the final extrusion step is varied in each batch. The final pore sizes in each case are 0.2, 0.1, and 0.05 $\mu$m. The average values and variation coefficients of the results from three batches each are summarized in Table 10.

TABLE 10

Properties of Gd-DTPA-Containing Liposomes as a Function of Pore Size

| Example | Pore Size | Average Diameter [nm] | Inclusion [%] |
|---|---|---|---|
| 58 | 0.20 | 158 | 50.1 ± 2.8 |
| 59 | 0.10 | 113 | 46.3 ± 1.8 |
| 60 | 0.05 | 84 | 43.2 ± 0.4 |

Examples B 61–B 63: Gd-DTPA Inclusion and Vesicle Size as a Function of Lipid Concentration Batches are produced and characterized as under Example B 57, but with the difference that different lipid concentrations (100, 150, and 200 mg/ml) are used. The average values and variation coefficients of the results from three batches each are summarized in Table 11.

TABLE 11

Properties of Gd-DTPA-Containing Liposomes as a Function of Lipid Concentration

| Example | Lipid Concentration [mg/g] | Average Diameter [nm] | Inclusion [%] |
|---|---|---|---|
| 61 | 100 | 107 | 37.9 ± 0.8 |
| 62 | 150 | 101 | 49.5 ± 5.1 |
| 63 | 200 | 114 | 61.5 ± 0.9 |

Example B 64: Production of Liposomes with a Lipophilic Pharmaceutical (Methylprednisolone aceponate—MPA)

20 ml of placebo liposomes consisting of 50 mg of SPC/ml, which was produced according to Example 1, but with 0.2 $\mu$m as the final extrusion stage, is mixed with 50 mg of MPA and then stirred at room temperature for 24 hours with a magnetic stirrer.

The liposomes thus obtained have an average diameter of 189 nm with a variation coefficient of 30%. The MPA is completely encapsulated in the liposomes.

Example B 65: Production of a 5% O/W-Emulsion 1.5 g of lipoid E 80 is suspended in about 50 ml of bidistilled water, and then 5 ml of filtered soybean oil (both of Lipoid KG, Ludwigshafen) is added. After adding bidistilled water to make it up to 100 ml, the mixture is predispersed for 10 minutes with an Ultraturrax (13,500 rpm). Then, this predispersion is extruded 10 times each over two polycarbonate filters (0.1 $\mu$m) placed one above the other. The droplet size of the homogeneous, yellowish-cloudy O/W emulsion thus obtained is about 430 nm.

Example B 66: Production of a 5% O/W Emulsion Using a PTFE Filter 1.5 g of lipoid E 80 is suspended in about 50 ml of bidistilled water, and then 5 ml of filtered soybean oil (both of Lipoid KG, Ludwigshafen) is added. After adding bidistilled water to make it up to 100 ml, the mixture is predispersed for 10 minutes with an Ultraturrax (13,500 rpm). Then, this predispersion is extruded 10 times each over two PTFE filters (0.2 $\mu$m) placed one above the other. The droplet size of the homogeneous, yellowish-cloudy O/W emulsion thus obtained is about 230 nm.

Example B 67: Production of a 20% O/W Emulsion 1 g of cremophor S9 (BASF) is suspended in about 50 ml of bidistilled water and then 20 ml of filtered soybean oil (Lipoid KG, Ludwigshafen) is added to it. After adding bidistilled water to make it up to 100 ml, the mixture is predispersed for 1 minute with an Ultraturrax (8000 rpm). Then, this predispersion is extruded 10 times each over two polycarbonate filters (0.1 µm) placed one above the other. The droplet size of the homogeneous, milky-cloudy O/W emulsion thus obtained is about 880 nm.

What is claimed is:

1. A process for the production of a liquid, disperse system, comprising continuously not batchwise extruding a predispersion comprising water and lipids, liposomes or both under a pressure of 7 to 250 MPa sequentially through 1 to 8 filter stages each stage having a pore diameter of from 0.01 to 35 µm wherein at least one filter in a filter stage is a membrane filter.

2. The process according to claim 1, wherein at least one filter in a filter stage is made of an inorganic material.

3. The process according to claim 1, wherein each filter stage contains 2 to 4 membrane filters, placed one above the other.

4. The process according to claim 3, wherein the filters placed one above the other have different pore sizes.

5. The process according to claim 1, wherein there is more than one filter stage and the filter stages are sequentially of decreasing pore size.

6. The process according to claims 1, wherein extruding is conducted for 1 to 20 passages through the filter stages.

7. The process according to claim 1, wherein the amount of liquid, disperse system product produced in one operation is above 100 ml.

8. The process according to claim 1, wherein the flow of liquid, disperse system product is more than 150 ml per minute.

9. The process according to claim 1, wherein the liquid, disperse system is an emulsion.

10. The process according to claim 1, wherein the liquid, disperse system is a liposome suspension.

11. The process according to claim 10, wherein the liposomes contain x-ray contrast media.

12. The process according to claim 11, wherein the liposomes contain iotrolan, iopromide, or 3-carbamoyl-5-[N-(2-hydroxyethyl)-acetamido]-2,4,6-triiodobenzoic acid-[(1RS,2SR)-2,3-dihydroxy-1-hydroxymethylpropyl]-amide, as the x-ray contrast media.

13. The process according to claim 10, wherein the liposomes contain NMR contrast media.

14. The process according to claim 13, wherein the liposomes contain Gd-DTPA, Gd-EOB-DTPA, or gadobutrol as the NMR contrast media.

15. The process according to claim 9, wherein the emulsion is sterile.

16. The process of claim 10, wherein the liposome suspension is sterile.

17. A device for the production of a liquid, disperse system comprising a storage vessel having a drainpipe leading to a high-pressure pump, said pump providing a working pressure of from 7 to 250 MPa, and said pump being in communication with a filter holder for 1 to 8 filter stages, each with a pore diameter of 0.01 to 35 µm, at least one filter in a filter stage being a membrane filter, such that material from the storage vessel is continuously not batchwise pumped through the filter stage(s), and means by which the product liquid, disperse system can be recirculated to the filter stage(s), removed from the device, or both.

18. A device according to claim 17, wherein the high-pressure pump provides a working pressure of from 7 to 80 MPa.

19. The device according to claim 17, additionally comprising a prefilter holder mounted between the high-pressure pump and filter holder for filters with an average pore size of 2 to 35 µm.

20. A device according to claim 17, additionally comprising a ventilating device, a temperature and pressure gauge or both.

21. The process of claim 1, wherein the pressure is 7 to 80 MPa.

22. The process according to claim 1, wherein the predispersion is extruded through at least one PTFE filter.

23. The process according to claim 1, wherein the liquid, disperse system contains liposomes prepared from a predispersion containing lipids.

24. The process of claim 23, wherein the lipid concentration in the predispersion is 400 mg/ml or higher.

25. The process of claim 23, wherein the lipid concentration in the predispersion is 500 mg/ml or higher.

26. The process of claim 1, wherein the liquid, disperse system produced has a gel-like consistency.

27. The process of claim 10, wherein the liposome suspension contains contrast medium encapsulated in liposomes and contrast medium unencapsulated in suspension and the unencapsulated contrast medium is not separated from the liposome suspension.

28. The process of claim 27, wherein the contrast medium contains iopromide.

29. A process for the production of pharmaceutical substance-containing liposomes comprising mixing a liposome suspension prepared according to the process of claim 10, wherein the liposomes contain no pharmaceutical substance, with a lipophilic pharmaceutical substance.

30. The process of claim 29, wherein the lipophilic pharmaceutical substance is methylprednisolone aceponate.

31. A process for the production of a liposome suspension wherein the liposomes contain a contrast medium, which comprises continuously, not batchwise extruding a predispersion comprising water and lipids, liposomes or both and the contrast medium under a pressure of 7 to 250 MPA sequentially through 1 to 8 filter stages each stage having a pore diameter of from 0.01 to 35 µm.

32. The process of claim 1, wherein the membrane filter is of a polymer membrane material.

* * * * *